United States Patent
Voor

[19]

[11] Patent Number: 6,159,210
[45] Date of Patent: Dec. 12, 2000

[54] BONE FIXATION PIN WITH ROTARY CUTTING TIP

[75] Inventor: Michael J. Voor, Louisville, Ky.

[73] Assignee: Research Corporation Technologies, Inc., Tucson, Ariz.

[21] Appl. No.: 09/052,790

[22] Filed: Jan. 14, 1998

Related U.S. Application Data

[60] Provisional application No. 60/036,096, Jan. 14, 1997.

[51] Int. Cl.$^7$ ................................................ A61B 17/56
[52] U.S. Cl. ............................................................ 606/56
[58] Field of Search ................................ 602/37, 16, 18; 606/61, 54, 90, 72, 104; D8/385–395

[56] References Cited

U.S. PATENT DOCUMENTS

| | | | |
|---|---|---|---|
| D. 264,807 | 6/1982 | Baumgartner | D8/387 |
| 1,398,842 | 11/1921 | Cruse . | |
| 2,393,982 | 2/1946 | Giesen . | |
| 2,494,792 | 1/1950 | Bloom | 606/56 |
| 2,966,383 | 12/1960 | Boetcker et al. | 606/56 |

(List continued on next page.)

FOREIGN PATENT DOCUMENTS

| | | | |
|---|---|---|---|
| 717968 A2 | 6/1996 | European Pat. Off. | A61B 17/60 |
| 2707863 | 1/1995 | France | A61B 17/68 |
| 41 20 393 C1 | 6/1992 | Germany | A61G 13/10 |
| 2101488A | 1/1983 | United Kingdom | A61B 17/18 |
| 2101488B | 1/1983 | United Kingdom | A61B 17/18 |
| WO96/17557 | 6/1996 | WIPO . | |

(List continued on next page.)

OTHER PUBLICATIONS

Hughes, (1995), "Cervical spine fractures," J.R. Coll. Surg. Edinb. 40(5):337–341.

Nickel, V.L. (1968), "The Halo. A Spinal Skeletal Traction Fixation Device," J. Bone and Joint Surg. 50–A(7):1400–1409.

(List continued on next page.)

*Primary Examiner*—Michael Buiz
*Assistant Examiner*—(Jackie) Tan-Uyen T. Ho
*Attorney, Agent, or Firm*—Greenlee, Winner and Sullivan, P.C.

[57] ABSTRACT

A fixation pin and methods for attaching an immobilizing device or frame to a bone or to the skull of a patient with a skeletal injury are provided. A preferred embodiment of the pin comprises an externally threaded cylindrical body having on its leading end a shoulder and a smaller diameter coaxial cylindrical post with a rotary cutting tip on its face. The post fits snugly into a hole drilled into the bone by the cutting tip without the need for a high axial force to insert and hold the post in place. Drilling the hole with a rotary cutting tip on the face of the post minimizes lateral damage to the bone. The minimal lateral bone damage and the low axial force provide for a low incidence of pin loosening and side effects such as infections secondary to loosening and headaches. The shoulder limits the depth of penetration of the cutting tip into the bone. A crescent shaped halo utilizing the fixation pin is also provided.

21 Claims, 9 Drawing Sheets

U.S. PATENT DOCUMENTS

| | | |
|---|---|---|
| 3,072,118 | 1/1963 | Standerwick et al. |
| 3,079,831 | 3/1963 | Gutshall .................................. D8/387 |
| 3,336,922 | 8/1967 | Taylor et al. |
| 3,358,548 | 12/1967 | Dyslin ..................................... D8/387 |
| 3,391,693 | 7/1968 | Georgiade et al. |
| 3,604,412 | 9/1971 | Gardner ..................................... 128/75 |
| 3,654,923 | 4/1972 | Crutchfield ............................ 128/84 R |
| 3,669,102 | 6/1972 | Harris ................................... 128/84 R |
| 3,877,424 | 4/1975 | Murray ................................. 128/92 A |
| 3,923,046 | 12/1975 | Heifetz .................................... 128/75 |
| 4,146,793 | 3/1979 | Bergstrom et al. .................... 250/444 |
| 4,244,360 | 1/1981 | Dohogne ............................... 128/92 A |
| 4,256,112 | 3/1981 | Kofp et al. ........................... 128/303 B |
| 4,308,863 | 1/1982 | Fischer ................................. 128/92 A |
| 4,350,159 | 9/1982 | Gouda .................................. 128/303 B |
| 4,360,012 | 11/1982 | McHarrie et al. ................... 128/92 EB |
| 4,393,868 | 7/1983 | Teague .................................. 128/92 A |
| 4,444,179 | 4/1984 | Trippi ..................................... 128/75 |
| 4,450,834 | 5/1984 | Fischer ................................ 128/92 EB |
| 4,456,004 | 6/1984 | Kenny .................................. 128/92 A |
| 4,465,069 | 8/1984 | Barbier et al. .......................... 128/303 |
| 4,475,550 | 10/1984 | Bremer et al. ...................... 128/303 B |
| 4,483,334 | 11/1984 | Murray ................................. 128/92 A |
| 4,502,473 | 3/1985 | Harris et al. ......................... 128/92 A |
| 4,564,007 | 1/1986 | Coombs et al. ...................... 128/92 A |
| 4,570,625 | 2/1986 | Harris et al. ......................... 128/92 G |
| 4,584,995 | 4/1986 | Koeneman ........................... 128/92 A |
| 4,612,930 | 9/1986 | Bremer ................................ 128/303 B |
| 4,620,533 | 11/1986 | Mears .................................... 128/92 Z |
| 4,667,660 | 5/1987 | Eingorn .................................... 602/37 |
| 4,730,608 | 3/1988 | Schlein .................................. 128/92 Z |
| 4,757,809 | 7/1988 | Koeneman et al. .................. 128/92 Z |
| 4,790,304 | 12/1988 | Rosenberg ............................ 128/92 Y |
| 4,838,264 | 6/1989 | Bremer et al. ...................... 128/303 B |
| 4,848,368 | 7/1989 | Kronner ................................ 128/92 Z |
| 4,895,141 | 1/1990 | Koeneman et al. ...................... 606/54 |
| 4,923,458 | 5/1990 | Fischer ..................................... 606/59 |
| 4,943,293 | 7/1990 | Lee, Jr. .................................... 606/96 |
| 4,968,316 | 11/1990 | Hergenroeder ............................ 606/90 |
| 4,969,886 | 11/1990 | Cziffer et al. ............................ 606/59 |
| 4,978,350 | 12/1990 | Wagenknecht ............................ 606/72 |
| 5,010,881 | 4/1991 | Boudreau et al. ..................... 128/76 R |
| 5,024,618 | 6/1991 | Tepic ........................................ 606/53 |
| 5,042,462 | 8/1991 | Bremer ................................... 128/75 |
| 5,112,331 | 5/1992 | Miletich .................................... 606/53 |
| 5,121,741 | 6/1992 | Bremer et al. ............................. 602/18 |
| 5,122,132 | 6/1992 | Bremer ..................................... 606/72 |
| 5,122,140 | 6/1992 | Ascne et al. ............................... 606/55 |
| 5,156,588 | 10/1992 | Marcune et al. .......................... 602/17 |
| 5,160,335 | 11/1992 | Wagenknecht ............................ 606/54 |
| 5,197,965 | 3/1993 | Cherry et al. ............................. 606/54 |
| 5,275,599 | 1/1994 | Zbikowski et al. ....................... 606/54 |
| 5,312,403 | 5/1994 | Frigg ........................................ 606/54 |
| 5,347,894 | 9/1994 | Fischer ..................................... 81/471 |
| 5,393,161 | 2/1995 | Mata et al. ............................... 403/133 |
| 5,403,322 | 4/1995 | Herzenberg et al. ..................... 606/98 |
| 5,443,464 | 8/1995 | Russell et al. ............................ 606/54 |
| 5,451,225 | 9/1995 | Ross, Jr. et al. .......................... 606/59 |
| 5,456,266 | 10/1995 | Brown ..................................... 606/56 |
| 5,490,832 | 2/1996 | Brown ..................................... 602/37 |
| 5,522,817 | 6/1996 | Sander et al. ............................ 606/72 |
| 5,792,142 | 8/1998 | Galitzer ................................... 606/72 |
| 5,908,422 | 6/1999 | Bresina .................................... 606/72 |

OTHER PUBLICATIONS

Ogon, M. et al. (1996), "Comparison Between Single–Screw and Triangulated, Double–Screw Fixation in Anterior Spine Surgery: A Biomechanical Test," Spine 21(23):2728.

Perry, J. et al. (1959), "Total Cervical–Spine Fusion of Neck Paralysis," J. Bone and Joint Surg. 41–A:37–59.

Rusanen, M. et al. (1985), "The halo brace in unstable fractures of the cervical spine: a review of 14 cases," Injury 16:318–320.

Whitesides, T.E. et al. (1992), "The Force Exerted by the Halo Pin," Spine 17:S413–S417.

Bremer Medical, Inc., brochure on Bremer Halo Systems, 16 pp. (double sided).

Bremer brochure, 4 pp. (double sided) (best copy available).

Ballock, R.T. (1990), "The Effect of Pin Location on the Rigidity of the Halo Pin–Bone Interface," Neurosurgery 26(2):238–241.

Botte, M.J. et al. (1996), "Halo Skeletal Fixation: Techniques of Application and Prevention of Complications," J. Am. Acad. Orthopaedic Surgeons 4:(1):44–53.

Garfin, S.R. et al. (1986), "Structural Behavior of the Halo Orthosis Pin–Bone Interface: Biomechanical Evaluation of Standard and Newly Designed Stainless Steel Halo Fixation Pins," Spine 11(10):977–981.

Glaser, J.A. et al. (1986), "Complications associated with the halo–vest," J. Neurosurg. 65:762–769.

Koch, R.A. Nickel, V.L. (1978), "An Evaluation of Motion and Forces Across the Neck," Spine 3:(2):103–107.

Manthey, D.E. (1994), "Halo Traction Device," Emergency Medicine Clinics of North America 12(3):771–778.

Smith, M.D. et al. (1996), "A Biomechanical Study of Torque and Accuracy of Halo Pin Insertional Devices," J. Bone Joint Surgery 78–A(2):231–238.

Voor, M.J. and Khalily, C., "Halo Pin Loosening: A Biomechanical Comparison of Experimental and Conventional Designs," manuscript, 21pp.

Ultra–X External Fixation System, brochure, 2pp.

Synthes—Fixateur Externe, (in German) brochure, 14pp.

Orthofix, brochure, 4pp.

Smith & Nephew Richards, HEX–FIX™, brochure, 4pp.

Bremer Halo System, brochure, 4pp.

PRIOR ART

PRIOR ART

BONE FIXATION PIN WITH ROTARY CUTTING TIP

CROSS-REFERENCE TO RELATED APPLICATIONS

This application takes priority under 35 USC § 119(e) to U.S. provisional application serial No. 60/036,096, filed Jan. 14, 1997, which is incorporated in its entirety by reference herein.

This invention relates generally to orthopedic instruments used in surgery and more specifically to pins for use in bone reparation.

BACKGROUND OF THE INVENTION

In cases of skeletal injuries such as broken bones and cervical spinal injuries, it is usually necessary to fix or stabilize the position of the bones or the head of a patient while the injury heals or undergoes treatment. Such fixation may require the attachment of an external fixation frame to the long bones or a traction device or halo orthosis to the skull of a patient. A commonly used device for attaching a frame to a bone structure is the fixation pin. The halo orthosis or halo traction device provides cervical spine immobilization by penetration of the outer table of the skull with fixation pins passed through a ring or "halo" surrounding the skull and attached to a rigid body vest or cast or to a traction mechanism. As used herein, "halo orthosis" refers to the entire support apparatus and "halo" refers to the ring or frame which fully or partially surrounds the skull. The external fixation frame provides long bone immobilization by penetrating each segment of the broken bone with fixation pins attached to a rigid frame.

Fixation pins are well known in the art. Typically, halo type fixation pins are screw-like devices having a threaded cylindrical body, a conical tip at the front end for penetrating at least the outer surface of a bone, and a head or depression at the rear end for coupling to a means for rotating the pin. Long bone fixation pins are typically threaded and may be self-tapping.

Many types of fixation pins have been devised and described in patents and publications. U.S. Pat. No. 2,966,383, to Carl H. Boetcker and William A. Shafer, 1960, discloses a surgical headrest utilizing a pin having a spring-loaded conical tip with a surrounding flange.

U.S. Pat. No. 4,978,350, to Marcel H. Wagenknecht, 1990, discloses a fixation pin having flutes similar to a twist drill cut into the threaded portion of the pin.

U.S. Pat. No. 5,522,817, to Thomas W. Sander and Jeffery S. White, 1996, discloses a surgical bone pin having a bone penetrating element and a bioabsorbable shaft of uniform diameter.

An article "Structural Behavior of the Halo Orthosis Pin-Bone Interface: Biomechanical Evaluation of Standard and Newly Designed Stainless Steel Halo Fixation Pins" by Steven R. Garfin et al. from Spine, Vol. 11, No. 10 of 1986, pages 977–981 contains FIGS. 1 and 2 on page 978 showing various pin designs. These two figures are reproduced herein as FIGS. 1A–1G and FIGS. 2A–2B, respectively. The alphabetic portions of the figure numbers for FIGS. 1A–1G and FIGS. 2A–2B herein correspond to the alphabetic reference characters in FIGS. 1 and 2 of the article.

FIGS. 1A–1G are schematic diagrams of one standard (control) pin design and six experimental pin designs: standard tip (FIG. 1A), conical tip (FIG. 1B), cylindrical tip with sharp cutting edge (FIG. 1C), cylindrical tip with sharp cutting teeth on edge (FIG. 1D), narrow bullet tip (FIG. 1E), wide bullet tip (FIG. 1F), and bullet tip and raised cylindrical shoulder with cutting edge FIG. (1G). The authors of the article stated that "All designs but one proved unsatisfactory because of inadequate (FIG. 1: C, D, E) or excessive (FIG. 1: B, G) pin penetration into the calvarium. The remaining pin design (FIG. 1: F, and FIG. 2) used a stainless steel cylindrical tip 1.5 mm in diameter with a sharp, slightly tapered point machined on the end. The distance from the tip of the pin to the shoulder measured 2.5 mm. The choice of this distance was based on previous measurements of the mean thickness of the outer cortex of the adult calvarium. This pin design enables the cylindrical column of the pin to penetrate the outer table of the adult calvarium, but further penetration is limited by the shoulder of the pin. As a result, adequate pin penetration is achieved but excessive penetration with its serious complications is avoided."

FIGS. 2A and 2B are schematic diagrams showing in greater detail the experimental wide bullet tip design of FIG. 1F and the standard tip design of FIG. 1A, respectively. The control pin having the standard tip design was described in the article as a commercially available stainless steel halo fixation pin (Jerome Medical, Mt. Laurel, N.J.).

With the potential for catastrophic complications associated with inadequate immobilization of unstable cervical spine injuries, it is important to maintain a stable connection between a halo and the skull of the patient. However, loosening of the fixation pins at the pin-bone interface is the most common complication associated with use of the halo orthosis. Pin loosening rates as high as 60% have been reported. Conclusions have typically been that loosening is reduced if the insertion torque and subsequent pin tip penetration are increased resulting in a larger axial pin fixation force into the skull surface.

Conventional conical or tapered pin tips require high axial forces to insert and hold the pins in place without loosening. For example, the aforementioned article states that a torque of 8 in-lb (0.9 N-m) applied to halo pins has been found to be safe and effective in lowering the incidence of pin loosening and infection. Eight in-lb of torque applied to a fixation pin can produce axial forces in the range of 100 to 200 pounds (450 to 900 N) depending on the material of the pin, lubrication, etc. Such high forces can be quite uncomfortable for the patient. For example, headaches are a well documented side effect of halo fixators.

It is therefore an object of this invention to provide a fixation pin which can be inserted and held in place with a small axial force and with little damage to the surrounding bone, and which can withstand repetitive transverse loading without loosening. Another object of the invention is to provide a halo orthosis which affords more comfort and better peripheral vision for the patient, greater flexibility in pin placement, and better access to the spine for treatment. A further object of the invention is to provide a method of attaching an external fixation frame to a long bone which reduces the risk of damage to tissue surrounding the bone.

SUMMARY OF THE INVENTION

The invention provides a rotary-cutting fixation pin for attaching an immobilizing device or frame to a bone or to the skull of a patient. The pin comprises a body, a cylindrical post attached to the body, a rotary cutting tip on the face of the post, and a shoulder extending radially outward from the base of the post. Herein, when referring to a post, "base" refers to the attached end and "face" refers to the unattached end of the post. Also herein, when referring to a body or post, the word "cylindrical" means having a generally cylindrical surface but does not exclude depressions, reliefs, flats or flutes cut or formed into the cylindrical surface. The rotary cutting tip comprises cutting edges extending radially outward on the face of the post. Herein, the phrase "extending radially outward" means extending outward from the axis of a cylinder along any path having a radial component in its vector, such as a diagonal or spiral path, and may also include an axial component. The body is preferably cylindrical in shape, with a body diameter greater than the post diameter, and attached coaxially to the post. Then, preferably, the shoulder extends from the diameter of the post to the diameter of the body. Also preferably, the body has screw threads along a portion of its length, for inserting and retaining the pin in a halo or long bone, and a coupling feature for rotating the pin.

During insertion, the pin is rotated and the cutting tip is advanced into the bone. The cutting tip drills a clean cylindrical hole into the bone without requiring a large axial force. The shoulder limits the depth of penetration of the post into the bone. After insertion, the cylindrical post fits snugly in the hole and no axial force is necessary to hold the post in place.

Eliminating the need for large axial forces to insert and retain the pin in halo applications permits the use of a more comfortable halo orthosis, reduces compression damage to the bone surrounding the pin, reduces loosening of the pin in the bone, and reduces the incidence of side effects such as infections secondary to loosening and headaches resulting from continuous large axial forces over long periods of time.

The invention also provides a horseshoe shaped crescent halo and a method of attaching a long bone fixation frame, both utilizing a fixation pin of this invention.

DESCRIPTION OF THE PREFERRED EMBODIMENT

Figure 1G:
FIGS. 1A–1G are schematic diagrams of various forms of prior art.
Figure 1F:
Figure 1E:
Figure 1D:
Figure 1C:
Figure 1B:
Figure 1A:
Figure 2A:
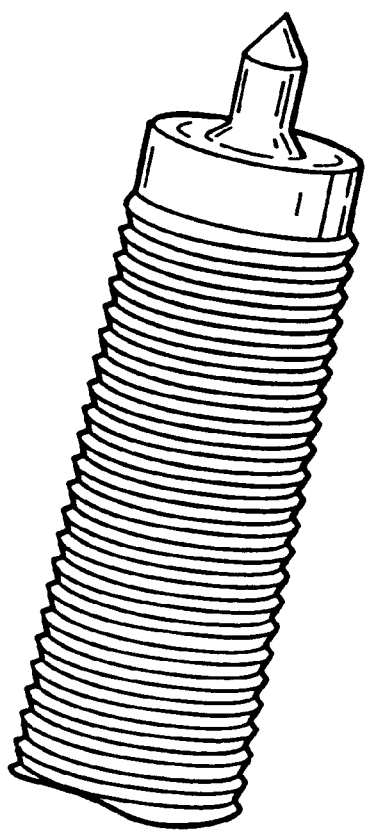
FIGS. 2A and 2B are more detailed diagrams of FIGS. 1F and 1A.
Figure 2B:
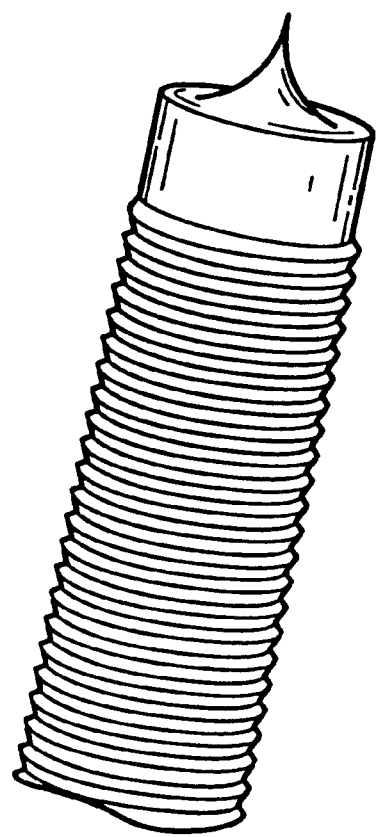

In the drawings, like reference numerals indicate like features; and, a reference numeral appearing in more than one figure refers to the same element.

The drawings and the following detailed descriptions show specific embodiments of the invention. Numerous specific details including materials, dimensions, and products are provided to enable a more thorough understanding of the invention.

However, it will be obvious to one skilled in the art that the present invention may be practiced without these specific details.

Figure 3:
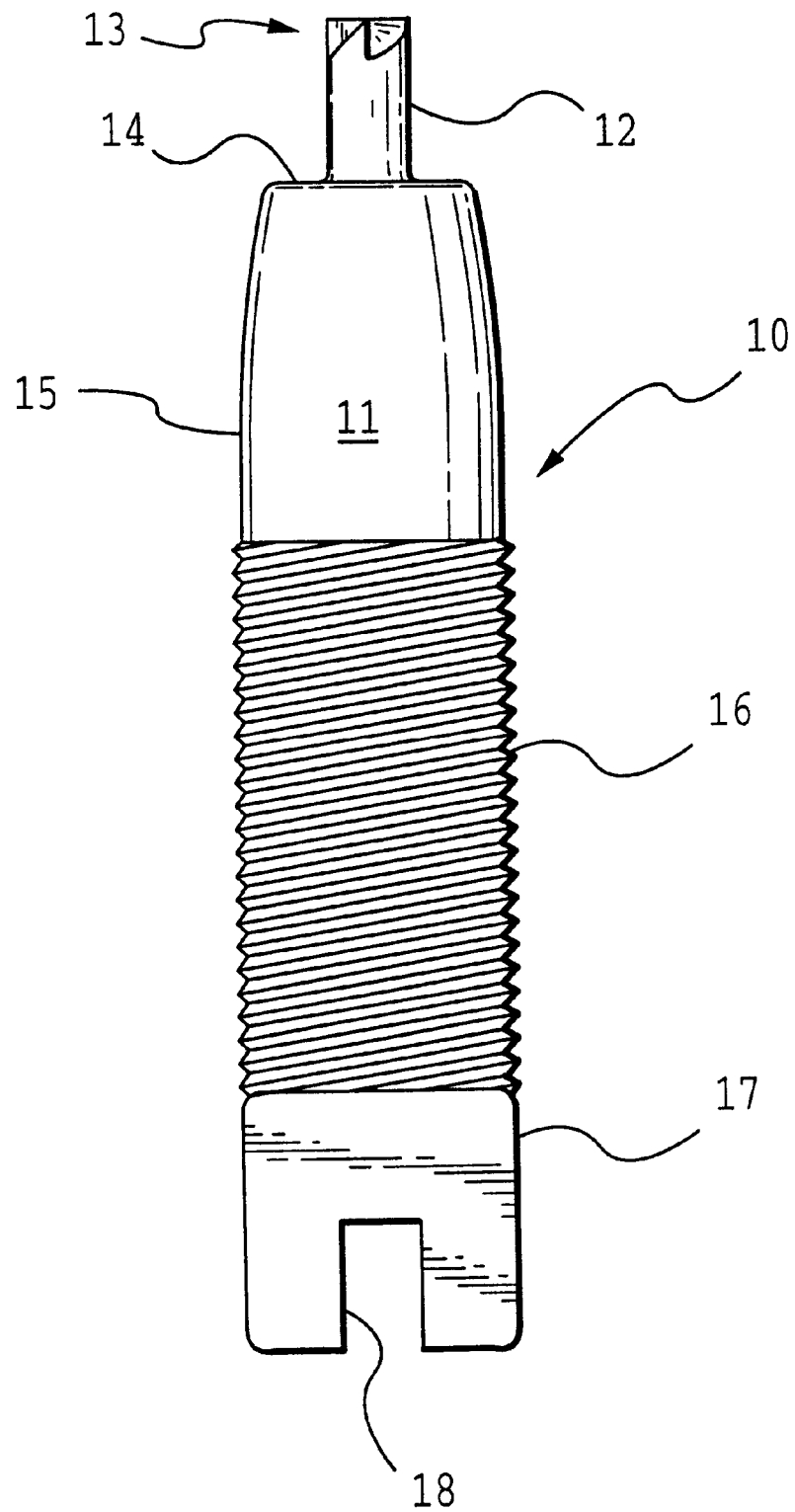
FIG. 3 shows a preferred embodiment of the fixation pin.

Referring to FIG. 3, fixation pin 10 comprises cylindrical body 11, cylindrical post 12 coaxially attached to the leading end of body 11, rotary cutting tip 13 formed on the face of post 12, radial shoulder 14 formed between the adjacent ends of the cylindrical surfaces of body 11 and post 12, optional screw threads 16 formed on a portion of the cylindrical surface of body 11, and optional square pin head 17 and screwdriver slot 18 formed on the trailing end of body 11. Preferably the post diameter is smaller than the body diameter and shoulder 14 extends between the post diameter and the body diameter. However, the diameter of shoulder 14 can be larger or smaller than than the diameter of body 11.

In use, when inserting pin 10 into a bone, pin 10 is rotated and cutting tip 13 is advanced into the bone by screw threads 16 or by an axial force applied to body 11. As cutting tip 13 advances, a hole is drilled into the bone which fits snugly around post 12. The drilling operation can be continued until shoulder 14 contacts the bone thereby limiting the depth of penetration of post 12 into the bone. By use of cutting tip 13 on the face of post 12, the bone outside the diameter of post 12 is undamaged by the insertion and retains its structural integrity for supporting transverse loads applied to post 12 and possible axial loads applied to shoulder 14.

The leading end of body 11 is optionally tapered. Tapered section 15 permits the use of a standard diameter for body 11, for strength and compatibility with existing frames, along with a smaller diameter for shoulder 14 to minimize the area of soft tissue involvement around the pin insertion site. However, the length, shape and degree of taper (including no taper) of section 15 may vary depending on various dimensions and applications of the pin. Pin head 17, comprising four flat surfaces formed on body 11, and screwdriver slot 18 comprise optional coupling features for rotating the pin during insertion. However, other forms of coupling features well known in the art may be used. For example, a hexagonal head comprising six flat surfaces formed within the diameter of body 11 may be used instead of square head 17 or a Phillips screwdriver or Allen wrench socket can be used in place of the flat blade screwdriver slot 18. Or, either the head or the slot can be used without the other. As a further example, an external cap can be threaded or clamped onto the pin thereby requiring no coupling feature at all.

Figure 4:
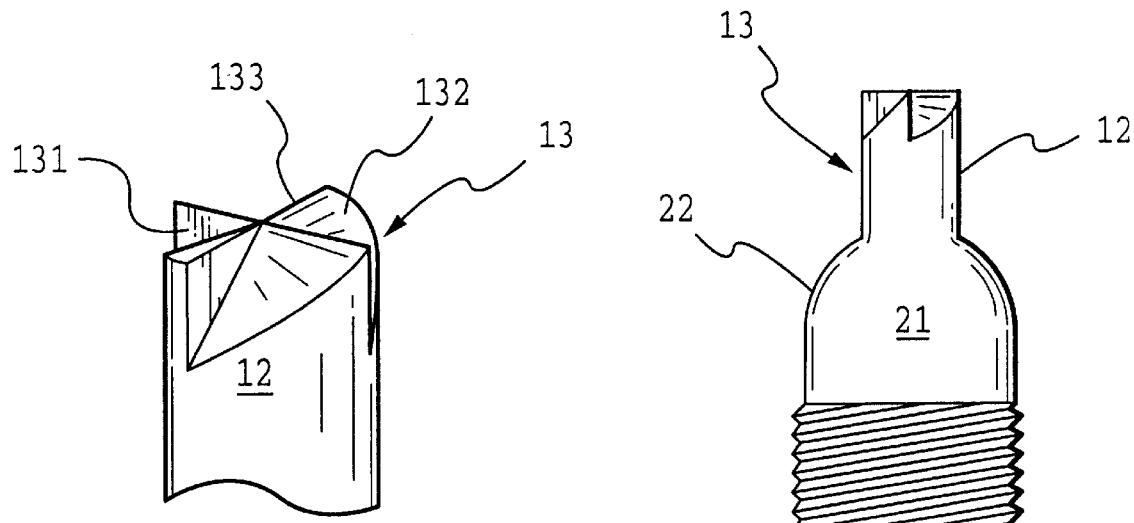
FIG. 4 is a perspective view of the rotary cutting tip of the pin.

FIG. 4 is an expanded perspective view of rotary cutting tip 13 showing rotationally leading surfaces 131, rotationally trailing surfaces 132, and cutting edges 133 formed by the intersections of surfaces 132 and 133. Cutting edges 133 extend radially outward to substantially the same radius as that of post 12 to permit cutting a clean hole which fits snugly around post 12. The open space between surfaces 131 and 132 provides room for bone chips as cutting progresses. Since bone is porous, the chips occupy less space than solid bone and spiral flutes such as used in twist drills are normally not necessary. However, within the definition of cylindrical as used herein, flutes may be provided on post 12 if necessary or desired. Although four cutting edges oriented substantially perpendicular to the axis of post 12 are shown here as a preferred embodiment, it will be apparent to those of ordinary skill in the art that the cutting function can be achieved with a different number, shape or orientation of cutting edges and surfaces. For example, the cutting edges can extend axially farther out at the center of the face than at the perimeter thereby forming a point similar to that of a twist drill.

Figure 5B:
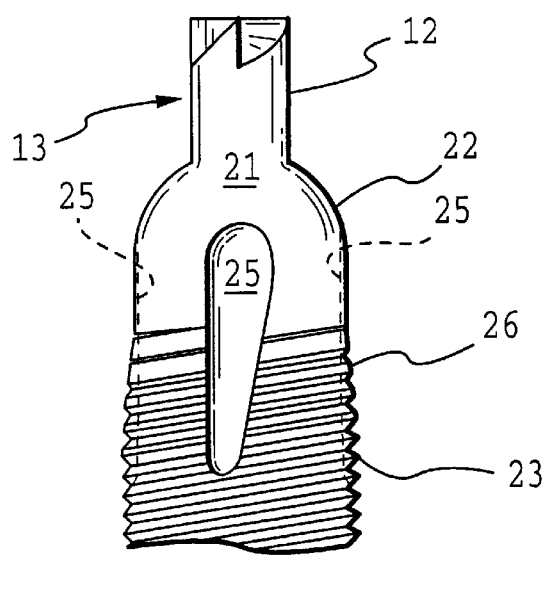
FIGS. 5A and 5B show variations on the embodiment of FIG. 3.
Figure 5A:
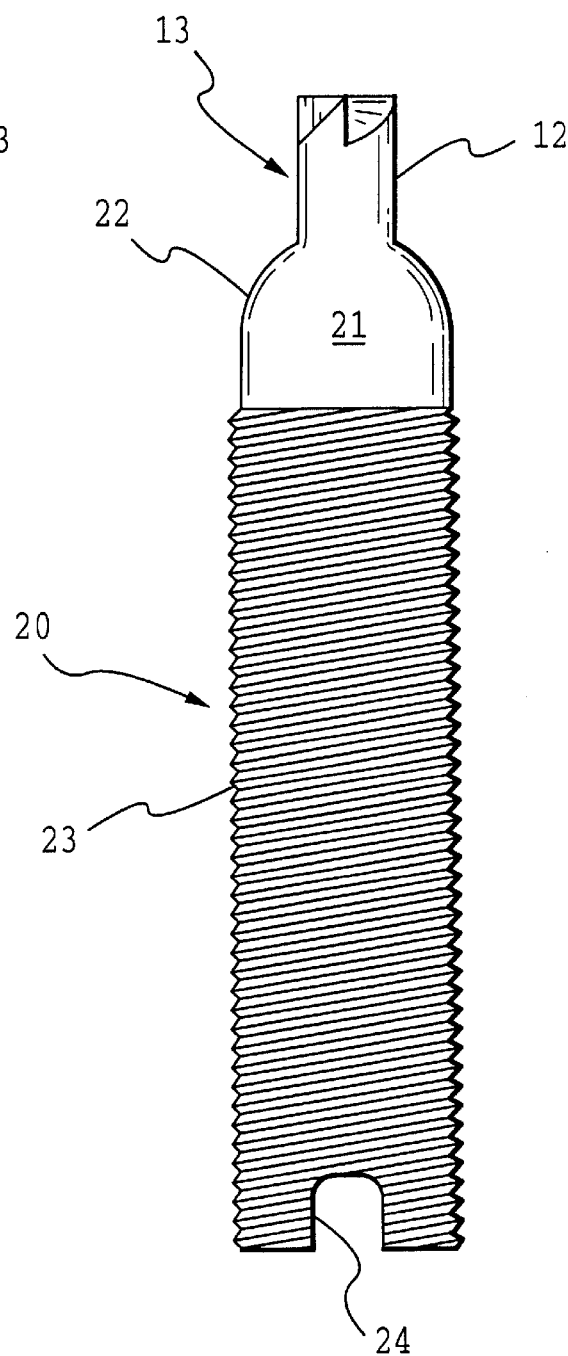

FIG. 5A shows a variation on the configuration of fixation pin 10 of FIG. 3. Fixation pin 20 comprises cylindrical body 21, cylindrical post 12 coaxially attached to the leading end of body 21, rotary cutting tip 13 formed on the face of post 12, rounded shoulder 22 formed between the adjacent ends of the cylindrical surfaces of body 21 and post 12, screw threads 23 formed on a portion of the cylindrical surface of body 21 and screwdriver slot 24 formed on the trailing end of body 21. In this configuration, shoulder 22 flows smoothly from the cylindrical surface of body 21 to a surface substantially perpendicular to the axis common to body 21 and post 12. Also, the coupling feature consists of screwdriver slot 24 alone without the head 16 of FIG. 3.

Body 21 (and body 11 of FIG. 3) may be provided with flutes 25 and self-tapping threads 26 as shown in FIG. 5B for use in long bones (described later) or without threads for use in unthreaded immobilizing devices, e.g., devices with clamps for holding the pins. Self-tapping threads 26 can have the form of a truncated cone in that the diameters of the threads decrease toward the leading end. Although body 21 and body 11 of FIG. 3 are preferably cylindrical in shape, the cylindrical surface can be modified by flutes, flats or other surfaces contained within the diameter of the cylinder. For example, a coupling feature can be formed by grinding flat surfaces on a cylindrical body for receiving a wrench. Also, for example, a pin can include surfaces, such as flats, ground or otherwise formed on all or a portion of the length, and a portion of the circumference, of a cylindrical body (for receiving a tool such as an open end wrench) while retaining enough of a cylindrical shape to fit snugly into a round or threaded hole. If the fixation pin is not required to fit into a hole in a frame or orthosis, i.e., other devices for attaching the pin to the frame are used, the body of the pin may take whatever shape is appropriate for the attaching device. For example, the attaching device can be a screw or pin inserted through the frame and into the fixation pin.

Although the post, cutting tip, body and shoulder are described and illustrated in FIGS. 3, 4, 5A and 5B as integral parts of a pin, they can comprise discrete components fastened together to form a pin. For example, the shoulder can be a collar, flange or short ring formed on, or attached to, the base of the post. In this case, the post and the body adjacent to the post can have the same diameter with the shoulder having a larger diameter and thereby defining the base. Or, the shoulder can have the form of a disk captured or bonded between a discrete post and body.

Figure 6:
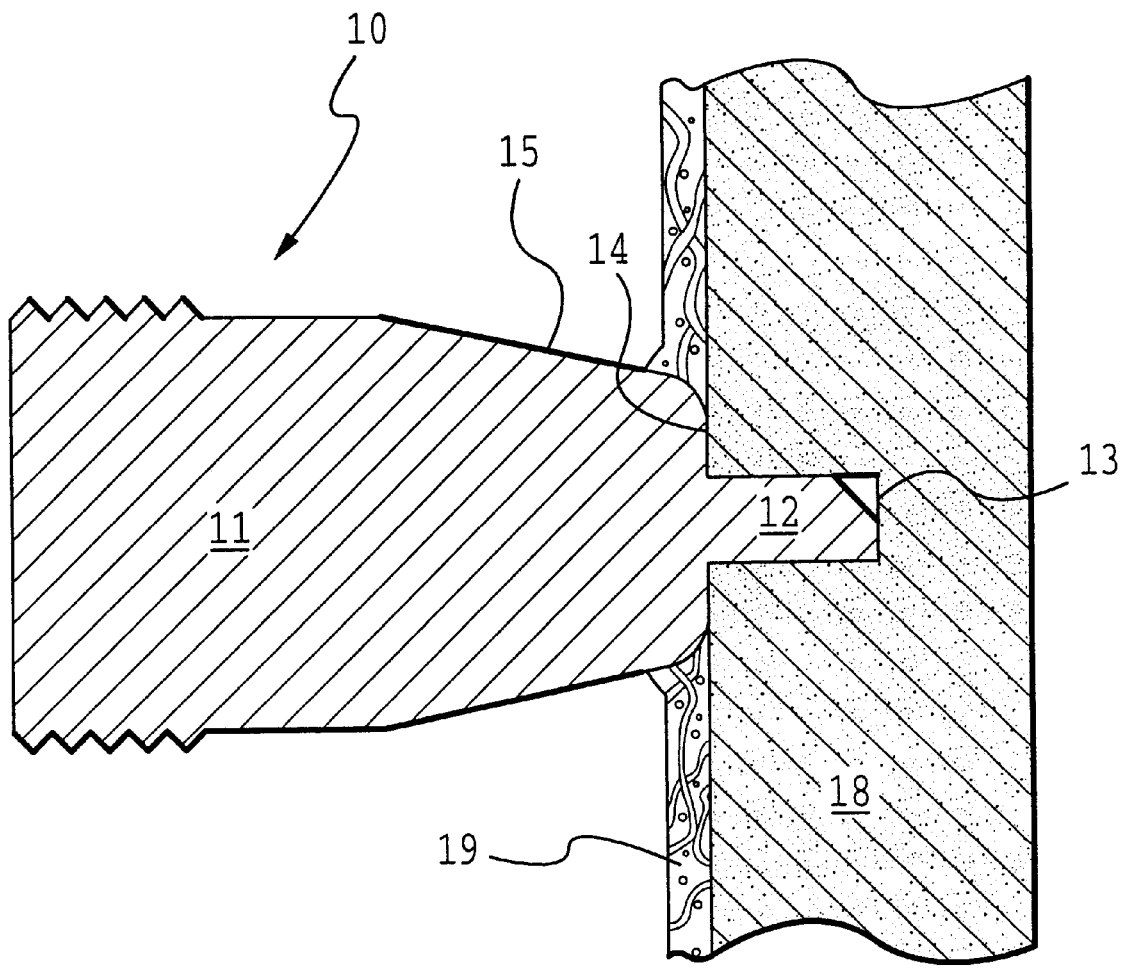
FIG. 6 is a cross-sectional side view of the pin in a skull.

FIG. 6 is a cross sectional view of fixation pin 10 inserted into a skull. This view shows post 12 of pin 10 inserted, through a small incision made in the external soft tissue 19 (skin), into skull 18. Preferably, during insertion, a halo (not shown) is placed around the head of the patient and body 11 is threaded into a tapped hole in the halo. Then pin 10 is rotated via its coupling feature, which advances cutting tip 13 into skull 18. This process cuts a clean cylindrical hole into skull 18 and leaves post 12 fitting snugly in the hole with minimal surrounding bone damage and with little or no required axial force. Alternatively, an unthreaded pin can be inserted into an unthreaded hole in a halo and rotated by a chuck clamped to the trailing end of the pin. The pin can be advanced by a low axial force applied to the pin by the chuck.

When the cutting process is finished, the pin can be held in place by a clamping device in the halo. In either case, if necessary, shoulder 14 limits the depth of penetration of cutting tip 13 by contact with the outer surface of skull 18.

Figure 7A:
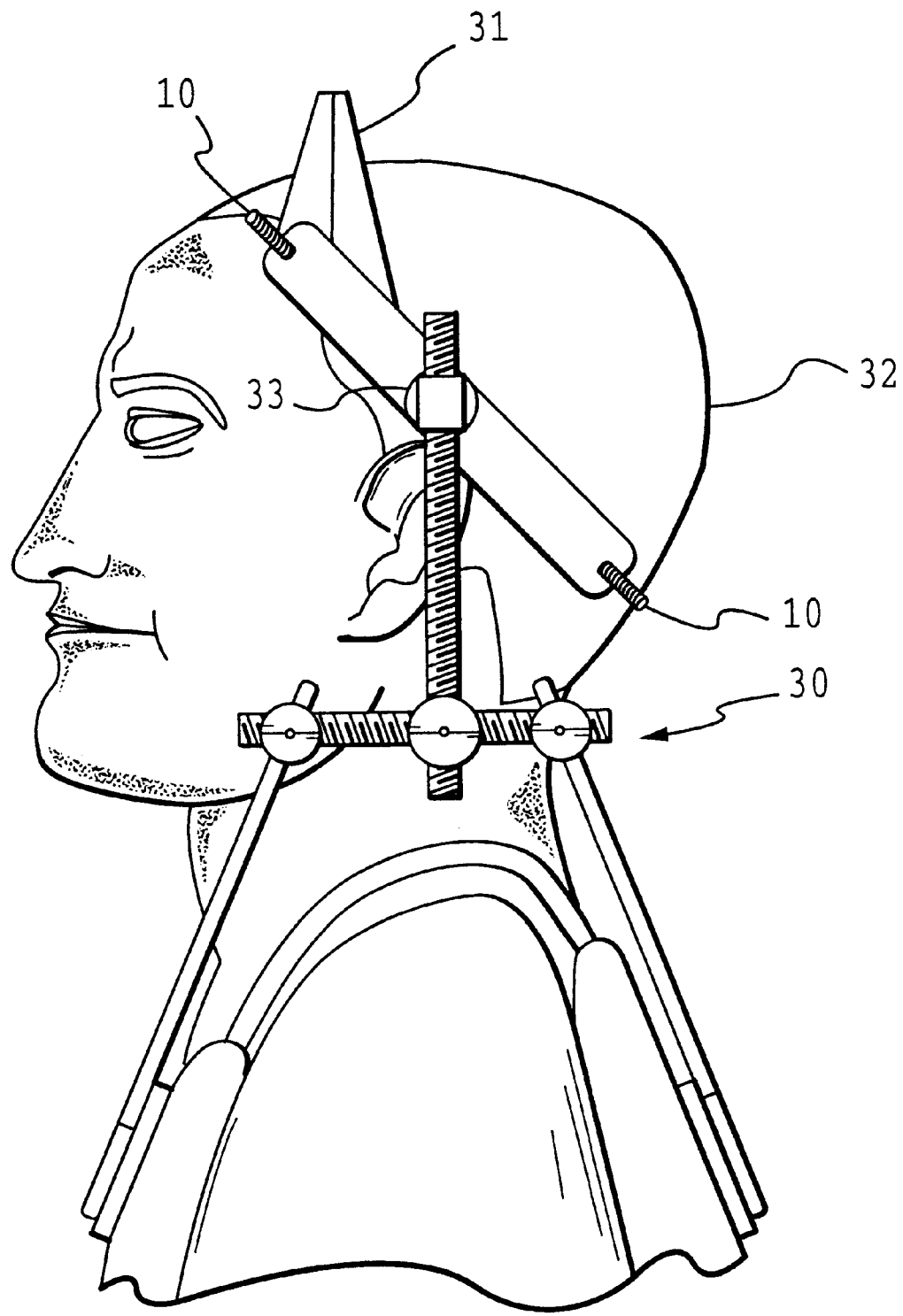
FIGS. 7A–7C show a crescent halo orthosis.

Because of the high axial force required to insert and prevent loosening of conventional fixation pins with conical or tapered tips, the halo portion of a halo orthosis is typically a complete, i.e., closed, ring and normally located on or near the equator of the skull to avoid slippage. The closed ring is more rigid when subjected to radial forces than an open ring of similar proportions and the skull is stronger near the equator. However, a closed ring at the equator location obstructs the peripheral vision of the patient, is uncomfortable and may limit access to the injured spine. In the current invention, the low axial force required by the fixation pin and its more effective penetration and increased fixation strength permit greater freedom in the shape and positioning of the halo. FIG. 7A is a schematic diagram of a crescent halo orthosis 30 made practical by fixation pin 10. Halo orthosis 30 includes crescent halo 31 which has the shape of an elongated crescent or horseshoe. Halo 31 is tilted backward relative to the equator of skull 32. Tilting halo 31 backward removes the peripheral vision limitation and moves the front pin insertion sites from the forehead to points behind the hairline where scarring is less evident. Because of the low axial force requirements of fixation pins 10, halo 31 does not need to be a complete circle and can be open at the back of skull 32. The open back of halo 31 provides more comfort for the patient and better access to the injured spine by the surgeon and other medical personnel. Halo 31 can be mounted on a lockable pivot 33 to permit tilting halo 31 to an angle appropriate for each patient. Although halo 31 is shown attached to a vest type orthosis, it can also be used with traction devices (not shown) and other orthoses known in the art.

Figure 7B:
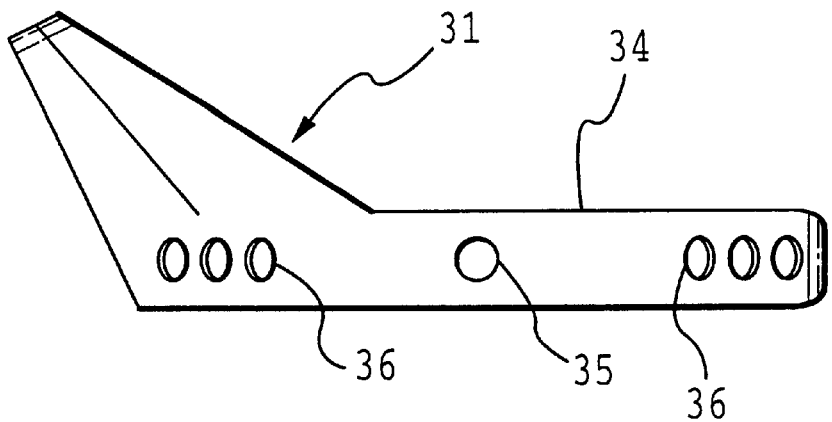
Figure 7C:
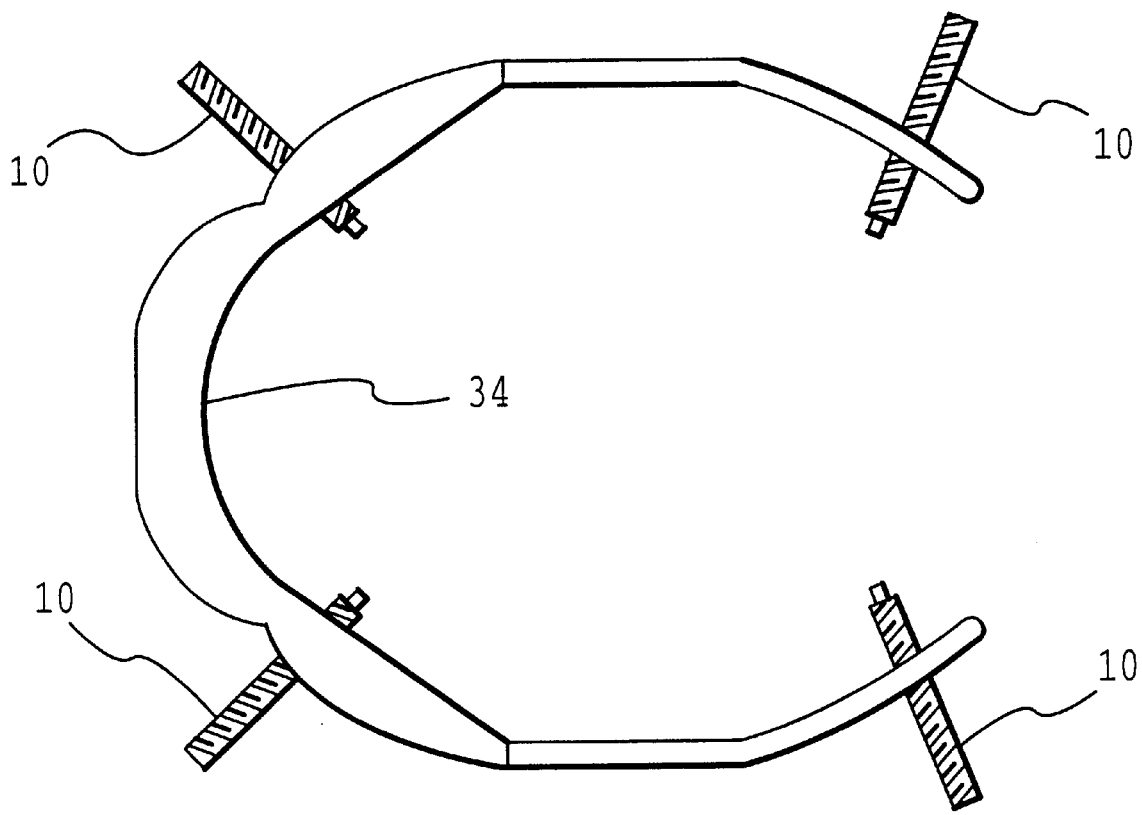

FIGS. 7B and 7C show side and plan views, respectively, of crescent halo 31. Halo 31 comprises frame 34 having a pivotal mounting feature 35 and multiple fixation pin holes 36. Halo 31 is mounted via feature 35 on lockable pivot 33 of FIG. 7A or on a traction device (not shown). Halo 31 can be rotated about pivot 33 for initial adjustment and then locked in place by pivot 33 to immobilize the spine. Multiple fixation pin holes 36 provide flexibility in locating pins 10 on the skull.

Figure 8:
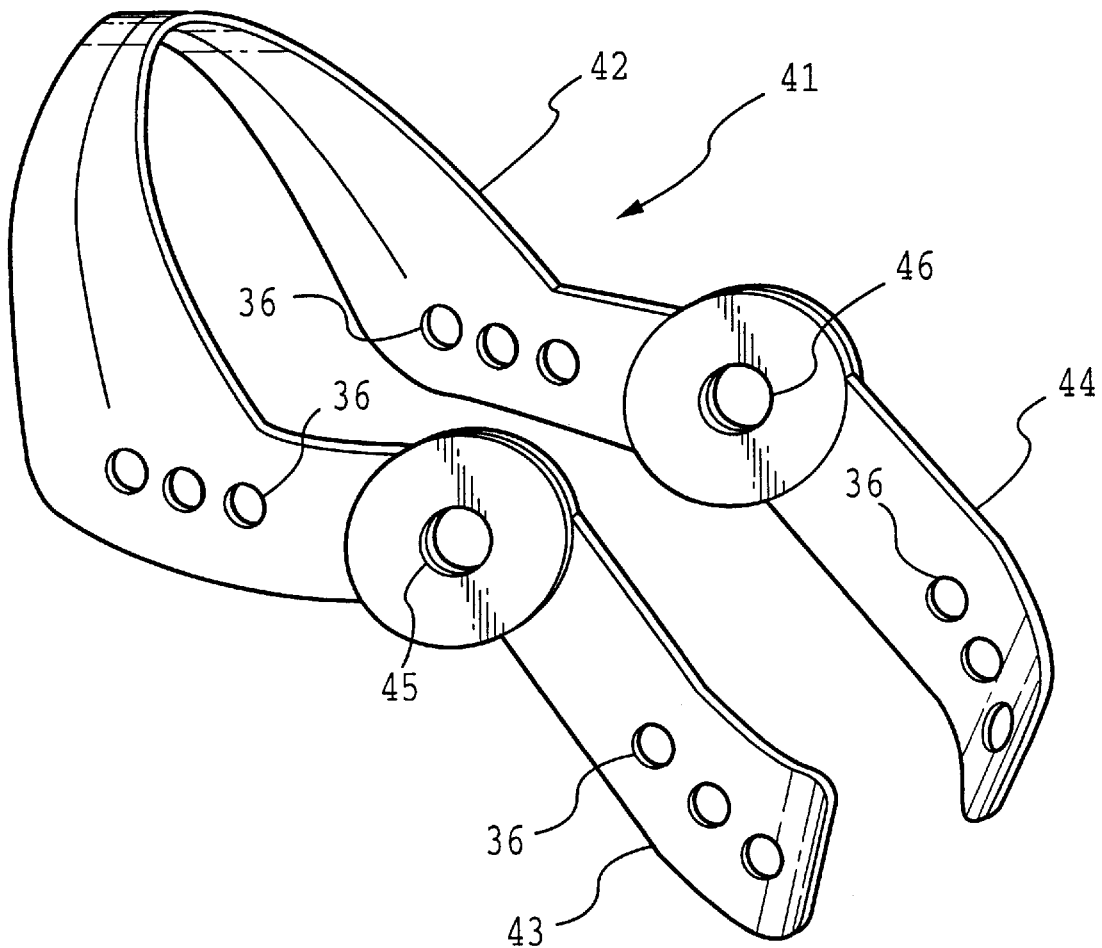
FIG. 8 shows a flexible halo orthosis.

A variation on the crescent halo is shown in FIG. 8. Flexible halo 41 comprises front section 42 and left and right side sections 43 and 44, each independently adjustable. Multiple fixation pin holes 36 provide flexibility in locating the pins on the skull. Sections 42, 43 and 44 include flexible mounting features 46 and 47 for attaching to a lockable pivot 33 as shown in FIG. 7A or to a traction device (not shown). Sections 42, 43 and 44 can be rotated about pivot 33 to fit halo 41 to the skull and then locked in position by lockable pivot 33 to immobilize the spine.

Figure 9A:
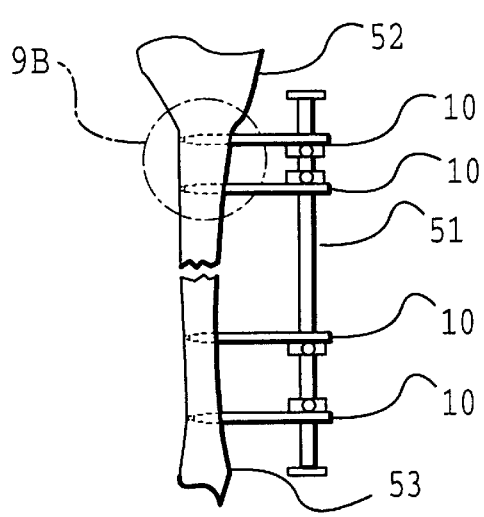
FIGS. 9A and 9B show the pin in a long bone application.
Figure 9B:
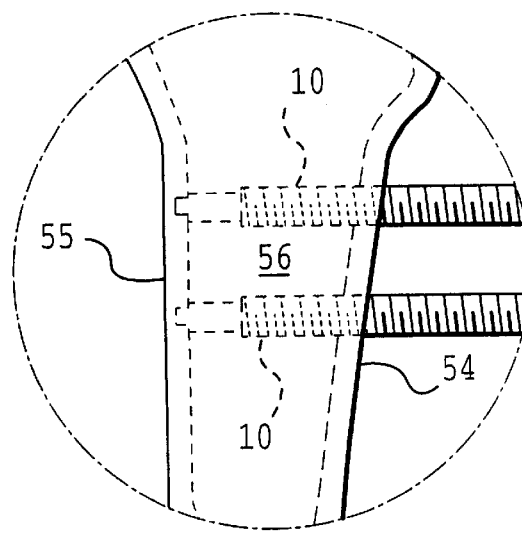

FIG. 9A is a schematic diagram of fixation pins 10 inserted into a long bone. A bone broken into two sections 52 and 53 is immobilized by external fixation frame 51 and fixation pins 10. FIG. 9B is an enlarged view of the encircled portion of FIG. 9A showing the pin insertion in greater detail. During insertion, holes slightly smaller than the outside diameter of pins 10 are drilled into a first side 54 of bone section 52 (or 53). Then pins 10 are threaded into side 54, utilizing self-tapping threads, and advanced by rotation through the interior 56 to second side 55 of section 52. Then, each pin 10 is further rotated, advancing cutting tip 13 into side 55. This process cuts a clean cylindrical hole into side 55 and leaves post 12 fitting snugly in the hole. Shoulder 14 limits the depth of penetration of cutting tip 13 into side 55. This method of attaching an external fixation frame to a long bone eliminates the risk of damage to tissue outside of bone side 55 caused by drilling and threading a conventional fixation pin through both sides 54 and 55 of bone section 52 (and 53). After pins 10 are inserted into bone sections 52 and 53, they are clamped into frame 51 by conventional methods.

Figure 10A:
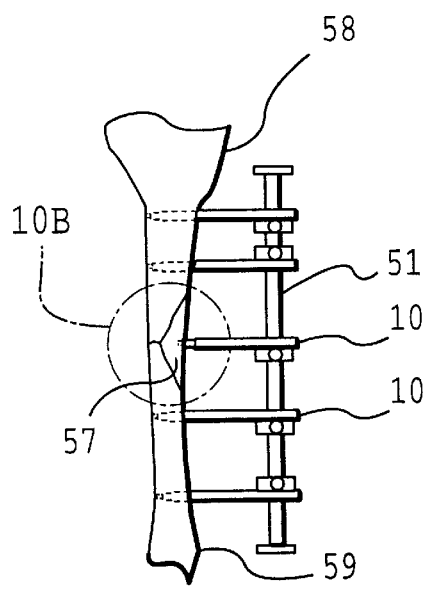
FIGS. 10A and 10B show the pin in a bone fragment.
Figure 10B:
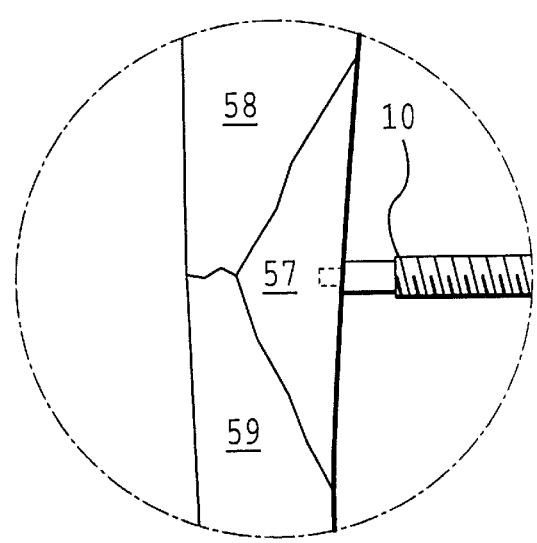

FIG. 10A is a schematic diagram of fixation pins 10 used to stabilize a bone fragment in a long bone. A bone broken into a fragment 57 and two sections 58 and 59 is immobilized by external fixation frame 51 and fixation pins 10. FIG.ure 10B is an enlarged view of the encircled portion of FIG. 10A showing the pin insertion into the fragment in greater detail. In this method, frame 51 is attached to bone sections 58 and 59 as described in FIGS. 9A and 9B. Then fixation pin 10 is threaded through a tapped hole in frame 41 and advanced by rotation through the external tissue (not shown) to the surface of fragment 57. Pin 10 is further rotated and cutting tip 13 is advanced into fragment 57 until shoulder 14 presses against the surface of fragment 57 thereby holding fragment 57 in place.

Although for simplicity in the drawings, FIGS. 6–10B all illustrate the use of pin 10 of FIG. 3, pin 20 of FIGS. 5A and 5B can be used in these applications, and may be preferred in the long-bone applications of FIGS. 9A–10B.

Empirical data indicate that the fixation pin of this invention withstands transverse cycling loads at an axial pin force of 50–90 N (11–20 lb) as well as conventional pins with conical tips withstand those loads at an axial pin force of 800–900 N (180–202 lb). Measured mean transverse force for single load failure of the pin of this invention was about 1000 N (225 lb) compared to about 550 N (124 lb) for conventional pins at an axial force of 50–90 N for both pins.

In summary, the invention provides a bone fixation pin having on its leading end a shoulder attached to a cylindrical post with a rotary cutting tip on its face. During insertion, the cutting tip cuts a clean cylindrical hole into a bone and the shoulder limits the depth of penetration. After insertion, the post fits snugly in the hole without requiring axial force for retention. The pin insertion causes minimal damage to bone surrounding the hole. Low axial force is needed to insert or hold the pin in place compared to conventional halo pins. The invention also provides a horseshoe-shaped crescent halo and a method of attaching an external fixation frame, both utilizing the fixation pin of this invention.

While the invention has been described above with respect to specific embodiments, it will be understood by those of ordinary skill in the art that various changes in form and details may be made therein without departing from the spirit and scope of the invention.

What is claimed is:

1. A bone fixation pin, comprising:
   a cylindrical post having a post diameter, a base and a face;
   a rotary cutting tip formed on said face;
   a shoulder extending radially outward from said base; and
   a body attached to said base.

2. The fixation pin of claim 1 wherein said cutting tip comprises a cutting edge formed by an intersection of a rotationally leading surface and a rotationally trailing surface, said surfaces contained within said post diameter.

3. The fixation pin of claim 1 wherein said body includes a cylindrical section having a body diameter, said cylindrical section attached to said base coaxially with said post.

4. The fixation pin of claim 3 wherein said body includes a surface formed on said body within said body diameter.

5. The fixation pin of claim 3 wherein said shoulder comprises a flange.

6. The fixation pin of claim 3 further comprising a tapered section formed on said body adjacent to said shoulder, said shoulder having a shoulder diameter not limited to said body diameter.

7. The fixation pin of claim 3 further comprising a screw thread formed on said cylindrical section.

8. The fixation pin of claim 7 further comprising self-tapping flutes formed in said body.

9. The fixation pin of claim 7 wherein a portion of said screw thread has a truncated cone shape.

10. The fixation pin of claim 1 further comprising a coupling feature for rotating said fixation pin.

11. The fixation pin of claim 10 wherein said coupling feature is a screwdriver slot.

12. The fixation pin of claim 10 wherein said coupling feature comprises a surface formed on said body for connecting a rotating device to said pin.

13. The fixation pin of claim 7 wherein said rotary cutting tip has a diameter no greater than said post.

14. A bone fixation pin, comprising:
   a cylindrical post, having a base, a face and a post diameter;
   a rotary cutting tip formed on said face, said tip comprising a cutting edge formed by an intersection of a rotationally leading surface and a rotationally trailing surface, said surfaces contained within said post diameter; and
   a shoulder extending radially outward from said base; and
   a body having a cylindrical section with a body diameter, said cylindrical section attached coaxially to said post.

15. The fixation pin of claim 14 further comprising a tapered section formed on said body adjacent to said shoulder, said shoulder having a shoulder diameter not limited to body diameter.

16. The fixation pin of claim 14 further comprising a screw thread formed on said cylindrical section.

17. A method of attaching a halo to a skull, comprising the steps of:
   providing a fixation pin of claim 1
   placing the halo around the skull;
   inserting the pin through the halo;
   rotating and advancing the cutting tip into the skull; and
   securing the pin to the halo.

18. A method of attaching an external fixation frame to a bone, comprising the steps of:
   providing a fixation pin of claim I having a post diameter smaller than the body diameter, comprising:
   drilling a hole into a first side of the bone;
   threading the body into the hole;
   rotating and advancing the cutting tip into a second side of the bone; and
   attaching the pin to the frame.

19. The method of claim 18 wherein the screw threads are self-tapping.

20. A crescent halo, for attaching to a skull, comprising:
   a frame, for partially encircling said skull;
   a plurality of fixation pin holes in said frame for receiving and retaining a fixation pin according to claim 1; and
   a mounting feature on said frame for attaching said frame to an immobilizing device.

21. The crescent halo of claim 20 wherein said frame comprises a plurality of independently adjustable sections.

* * * * *

UNITED STATES PATENT AND TRADEMARK OFFICE
CERTIFICATE OF CORRECTION

PATENT NO. : 6,159,210
DATED : December 12, 2000
INVENTOR(S) : Michael J. Voor

Page 1 of 2

It is certified that error appears in the above-identified patent and that said Letters Patent is hereby corrected as shown below:

Column 4,
Line 46, delete "intersections of surfaces 132 and 133" and replace with -- intersections of rotationally trailing surfaces 132 and the adjacent rotationally leading surfaces --.

Column 5,
Line 9, delete "16" and replace with -- 17 --.
Lines 46, 50, 51, and 61, delete "18" and replace with -- 32 --.

Column 6,
Line 40, delete "47" and replace with -- 45 --.

Column 7,
Line 3, delete "FIG.ure" and replace with -- FIG. --.
Line 7, delete "41" and replace with -- 51 --.

Column 8, claim 18,
Line 45, delete "claim I" and replace with -- claim 1 --.

UNITED STATES PATENT AND TRADEMARK OFFICE
CERTIFICATE OF CORRECTION

PATENT NO. : 6,159,210
DATED : December 12, 2000
INVENTOR(S) : Michael J. Voor

It is certified that error appears in the above-identified patent and that said Letters Patent is hereby corrected as shown below:

Figure 6,
Please delete item "18" and instead label the skull as -- 32 --.

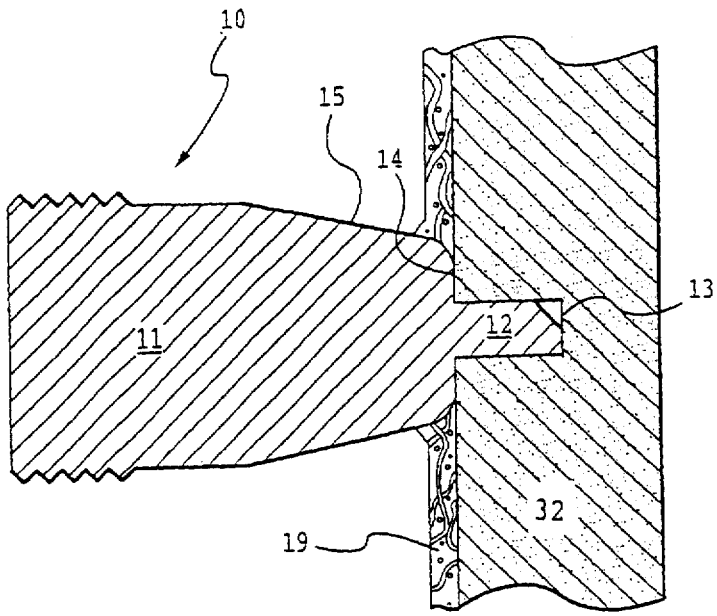

FIG.6

Signed and Sealed this

Eighteenth Day of December, 2001

Attest:

JAMES E. ROGAN
Attesting Officer    Director of the United States Patent and Trademark Office